US005573783A

United States Patent [19]

Desieno et al.

[11] Patent Number: 5,573,783
[45] Date of Patent: Nov. 12, 1996

[54] REDISPERSIBLE NANOPARTICULATE FILM MATRICES WITH PROTECTIVE OVERCOATS

[75] Inventors: Mark A. Desieno, Gilbertsville; Gregg Stetsko, Harleysville, both of Pa.

[73] Assignee: Nano Systems L.L.C., Collegeville, Pa.

[21] Appl. No.: 387,651

[22] Filed: Feb. 13, 1995

[51] Int. Cl.$^6$ ................................ A61K 9/16; A61K 9/50
[52] U.S. Cl. .................. 424/490; 424/484; 424/488; 424/489
[58] Field of Search ..................... 424/488, 489, 424/490, 484

[56] References Cited

U.S. PATENT DOCUMENTS

| | | | |
|---|---|---|---|
| 4,946,686 | 8/1990 | McClelland et al. | 424/473 |
| 5,118,528 | 6/1992 | Fessi et al. | 427/213.36 |
| 5,145,684 | 9/1992 | Liverside et al. | 424/489 |
| 5,308,620 | 5/1994 | Yen | 424/484 |
| 5,399,363 | 3/1995 | Liversidge et al. | 424/490 |

OTHER PUBLICATIONS

Lachman et al, "The Theory and Practice of Industrial Pharmacy", Chapter 2, "Milling", p. 45 (1986).
Martindale, "The Extra Pharmacopoeia, 29 edition", (1969).
Lieberman, Rieger, Baker, "Pharmaceutical Dosage Forms: Dispense Systems", vol. 1.

*Primary Examiner*—Thurman K. Page
*Assistant Examiner*—William E. Benston, Jr.
*Attorney, Agent, or Firm*—Rudman & Balogh

[57] ABSTRACT

A pharmaceutical film matrix comprising nanoparticles of a low solubility drug associated with a steric stabilizer and a film dispersing agent is coated on the surface of carrier particles and overcoated with a protective layer. Pharmaceutical compositions comprising the film matrix-coated carrier exhibit excellent bioavailability, are useful in methods of treating mammals and are extremely stable in that they are capable of being redispersed without extensive agglomeration into larger particles after being stored.

28 Claims, No Drawings

REDISPERSIBLE NANOPARTICULATE FILM MATRICES WITH PROTECTIVE OVERCOATS

FIELD OF THE INVENTION

This invention relates to film matrixes of nanoparticulate drug particles and pharmaceutical compositions containing them. The invention further relates to the use of and compositions for treating mammals.

BACKGROUND OF THE INVENTION

Bioavailability is the degree to which a drug becomes available to the target tissue after administration. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. Poorly water soluble drugs, i.e., those having a solubility less than about 10 mg/ml, tend to be eliminated from the gastrointestinal tract before being absorbed into the circulation. Moreover, poorly water soluble drugs tend to be unsafe for intravenous administration techniques, which are used primarily in conjunction with fully soluble drug substances.

It is known that the rate of dissolution of a particulate drug can increase with increasing surface area, i.e., decreasing particle size. Consequently, methods of making finely divided drugs have been studied and efforts have been made to control the size and size range of drug particles in pharmaceutical compositions. For example, dry milling techniques have been used to reduce particle size and hence influence drug absorption. However, in conventional dry milling, as discussed by Lachman, et al., *The Theory and Practice of Industrial Pharmacy*, Chapter 2, "Milling", p. 45 (1986), the limit of fineness is reached in the region of 100 microns (100,000 nm) when material cakes on the milling chamber. Lachman, et al. note that wet grinding is beneficial in further reducing particle size, but that flocculation restricts the lower particle size limit to approximately 10 microns (10,000 nm). However, there tends to be a bias in the pharmaceutical art against wet milling due to concerns associated with contamination. Commercial airjet milling techniques have provided particles ranging in average particle size from as low as about 1 to 50 μm (1,000–50,000 nm).

U.S. Pat. No. 5,145,684 discloses particles of a drug substance having a surface modifier absorbed on the surface thereof and methods for the preparation thereof by wet grinding. These particles have demonstrated significant pharmaceutical utility. Suitable surface modifiers described include various polymers. The surface modifiers disclosed include Pluronic F68 and F108, which are block copolymers of ethylene oxide and propylene oxide, Tetronic 908, which is a tetrafunctional block copolymer derived from sequential addition of propylene oxide and ethylene oxide to ethylene diamine; sodium dodecylsulfate, dialkyl esters of sodium sulfosuccinic acid such as Aerosol OT™, sodium lauryl sulfate, and Triton™ X-200. This patent notes the difficulty of forming nanoparticulate drug containing compositions which have good bioavailability and also are generally impervious to increase in size due to agglomeration of drug particles.

It is desirable to provide a pharmaceutical composition containing a nanoparticulate drug which can be stored for periods of time without undue loss of bioavailability due to agglomeration into larger size particles.

SUMMARY OF THE INVENTION

We have discovered stable film matrixes containing nanoparticulate drug particles which can be coated on to a carrier particle to be formulated into pharmaceutical compositions exhibiting high bioavailability.

More specifically, in accordance with this invention, there are provided pharmaceutical film matrices comprising nanoparticles of a low solubility drug associated with a steric stabilizer and a film dispersing agent wherein dissolution of the film results in substantial redispersion of the drug nanoparticles.

This invention also provides a stable pharmaceutical composition comprising a carrier particle having on its surface a film comprising nanoparticles of a low solubility drug associated with a steric stabilizer and a film dispersing agent, wherein dissolution of the film results in substantial redispersion of the drug nanoparticles.

In a particularly valuable and important embodiment of the invention there is provided a pharmaceutical composition comprising a carrier particle having on its surface a film comprising nanoparticles of a low solubility drug associated with a steric stabilizer and a film dispersing agent, wherein dissolution of the film results in substantial redispersion of the drug nanoparticles and an overcoat applied over said film comprising polyvinylpyrrolidone/polyethylene glycol (PVP/PEG).

The pharmaceutical compositions of this invention are useful in a method of treating mammals with a variety of drugs.

It is a particularly advantageous feature of this invention that the pharmaceutical compositions described herein exhibit high bioavailability.

Still another advantageous feature of this invention is that the compositions are stable against agglomeration of the drug nanoparticles into larger sizes because the compositions are readily redispersible.

Other advantageous features will become readily apparent upon reference to the following Description of Preferred Embodiments.

DESCRIPTION OF PREFERRED EMBODIMENT

This invention is based partly on the discovery that drug particles having an extremely small effective average particle size can be prepared by wet milling in the presence of grinding media in conjunction with a surface modifier, and that such particles are stable and do not appreciably flocculate or agglomerate due to interparticle attractive forces and can be formulated into pharmaceutical compositions exhibiting unexpectedly high bioavailability. While the invention is described herein primarily in connection with its preferred utility, i.e., with respect to nanoparticulate drug substances for use in pharmaceutical compositions, it is also believed to be useful in other applications such as the preparation of particulate dispersions for use in image and magnetic recording elements.

The particles of this invention comprise a drug substance. The drug substance exists as a discrete, crystalline phase. The crystalline phase differs from a noncrystalline or amorphous phase which results from precipitation techniques, such as described in EPO 275,796 cited above.

The invention can be practiced with a wide variety of drug substances. The drug substance preferably in present in an essentially pure form. The drug substance must be poorly soluble and dispersible in at least one liquid medium. By "poorly soluble" it is meant that the drug substance has a solubility in water of less than about 10 mg/ml and preferably less than about 1 part in greater than 1,000,000 parts of water. A preferred liquid dispersion medium is water. However, the invention can be practiced with other liquid media in which a drug substance is poorly soluble and dispersible including, for example, aqueous salt solutions, safflower oil and solvents such as ethanol, t-butanol, hexane and glycol. The pH of the aqueous dispersion media can be adjusted by techniques known in the art.

Suitable drug substances can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immuno-suppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics immunological agents lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators and xanthines. Preferred drug substances include those intended for oral administration and intravenous administration. A description of these classes of drugs and a listing of species within each class can be found in Martindale, The Extra Pharmacopoeia, Twenty-ninth Edition, The Pharmaceutical Press, London, 1989, the disclosure of which is hereby incorporated by reference in its entirety. The drug substances are commercially available and/or can be prepared by techniques known in the art.

Preferred and representative illustrative species of drug substances useful in the practice of this invention include danazol, naproxen and cylosporin.

The matrix of this invention comprises a steric stabilizer. The steric stabilizer is a hydrophilic or amphophilic compound having steric stabilizing properties such as a physical or chemical anchored molecule with backbone and side chains which import a physical barrier to interaction of the small particles. Examples of steric stabilizers can be found in Lieberman, Rieger, Banker *Pharmaceutical Dosage Forms: Disperse Systems,* Volume 1.

Preferred steric stabilizers are gelatin, casein, lecithin, gum acacia, cholesterol, tragacanth, sorbitan esters, polyoxyethylene alkyl esters, polyoxyethylene caster oil derivatives, polyoxyethylene, sorbitan fatty acid esters, polyethylene glycols, polyoxyethylene stearates, carboxymethylcellulose calcium, carboxymethylcellulose sodium, methylcellulose, hydroxyethylcellulose, hydroxypropylcellulose, hydroxypropylmethylcellulose, phthalate, non crystalline cellulose, polyvinyl alcohol and polyvinylpyrrolidone.

d-Alpha tocopheryl polyethylene glycol 1000 succinate is described by the manufacturer (Eastman Chemical Products, Inc., a division of Eastman Kodak Company, Kingsport, Tenn. 37622) in a product brochure dated Feb. 4, 1983 as "prepared from crystalline d-Alpha Tocopheryl Acid Succinate NF by esterification of the acid group with polyethylene glycol 1000", as also being named "Vitamin E TPGS", as being a "[p]ale yellow, waxy solid" having a specific gravity at 45° C. of approximately 1.06 and a melting point of approximately 40° C., and in the opinion of the manufacturer as being "recognized as safe ("GRAS")" when used as an oral dietary supplement of vitamin E."

The preferred amount of each of the cellulose derivative, polyethylene glycol or derivative thereof and waxy solid in the first composition of matter aspect of the invention is from about 5% to about 30% by weight of the coating composition.

The preferred amount of each of the hydropropyl methylcellulose, polyethylene glycol and polyoxyethylene-polyoxypropylene-polyoxyethylene block copolymer in the preferred first composition of matter aspect of the invention is from about 5% to about 15% by weight of the coating composition.

The most preferred steric stabilizer is polyvinylpyrrolidone.

The film matrix also comprises a film dispersing agent. The film dispersing agent is a water soluble compound associated with the surface of the nanoparticle. Film dispersing agents are those materials which oppose the binding capability of the film when placed in an aqueous environment enhancing film solubility or by swelling and disrupting films.

Preferred film dispersing agents are mannitol, sodium lauryl sulfate, mono and disaccharides. Sodium lauryl sulfate is particularly preferred. Sodium lauryl sulfate is also named as "[s]ulfuric acid monododecyl ester sodium salt; sodium starch glycolate; croscarmellose sodium" and "[s]odium monododecyl sulfate" and is described as . . . a mixture of sodium alkyl sulfates consisting chiefly of sodium lauryl sulfate [$CH_3(CH_2)_{10}CH_2OSO_3Na$]. The combined content of sodium chloride and sodium sulfate is not more than 8.0 percent.

In the dissolution step of the process aspect of the invention the temperature of warming can be in the range from room temperature to about 100° C. and is preferably in the range from 50° C. to 60° C. About 80% of the total amount of water needed is used for the dissolution and suspension steps and the remainder is used for rinsing the last amounts of solution and suspension from the equipment. Preferably the polyethylene glycol or derivative thereof and the waxy solid are dissolved first, and the cellulose derivative is then added and dissolved. The low solubility drug is added to the resulting solution with agitation to form a suspension. The dissolution and suspension steps are carried out with conventional mixing equipment. The suspension is preferably passed through a colloid mill before carrying out the coating step and agitation is maintained during the coating step. The coating and drying steps are preferably carried out in a fluid bed processor with inlet air temperature in the range from 50° C. to 70° C. with preheating of the sugar or sugar/starch beads. After drying the coated beads are sifted to produce coated beads of the desired particle size, preferably 16–60 mesh.

Preferred film matrices comprise nanoparticles of a low solubility drug having about 0.1% to about 60% of a steric stabilizer and about 0.05 to about 50% of a film dispersing agent, based on the weight of the low solubility drug, associated with the nanoparticle surface.

In a particularly preferred embodiment of this invention, the film matrix is overcoated with polyvinylpyrrolidone (PVP)/polyethylene glycol (PEG). This overcoat provides improved stability to the pharmaceutical composition.

The overcoating is prepared by casting PVP such as Providone with different types and units of PEG such as PEG 600, PEG 1000 and PEG 1450 and mixtures thereof. Polyethylene glycol is described as "an addition polymer of ethylene oxide and water, represented by the formula $H(OCH_2CH_2)_nOH$ in which n represents the average number of oxyethylene groups." The variants are designated by "nominal value" of "average molecular weight", which is explained as follows:

The average molecular weight is not less than 95.0 percent and not more than 105.0 percent of the labeled nominal value if the labeled nominal value is below 1000; it is not less than 90.0 percent and note more than 110.0 percent of the labeled nominal value if the labeled nominal value is between 1000 and 7000; it is not less than 87.5 percent and not more than 112.5 percent of the labeled nominal value if the labeled nominal value is about 7000.

Polyethylene glycols having nominal average molecular weights in the range from 300 to 8000 are described. Polyethylene glycol 3350 is the preferred polyethylene glycol of the invention.

Providone, USP is the USAN name for 2-Pyrrolodinone, 1-ethenyl-homopolymer of 1-vinyl-2pyrrolidinone polymer. It is sold under the trademarks KOLIDON (BASF), PLASDONE (International Specialty Products) and VINISIL (Abbott).

The weight ratio of PEG/PVP is generally from 1 to about 5. The pharmaceutical film matrix is formed by dissolving the PEG and PVP in a suitable solvent.

Suitable carriers comprise sugar spheres, maltodextrin, microcrystalline cellulose, microcrystal cellulose/sodium carboxylmethylcellulose, granular dextrose, dicalcium phosphate, tricalcium phosphate, mono and disaccharides. The preferred carriers are sugar spheres. Sugar Spheres are described as containing "not less than 62.5 percent and not more than 91.5 percent of surose ($C_{12}H_{22}O_{11}$), calculated on the dried basis, the remainder consisting chiefly of starch" and as consisting of "approximately spherical particles of a labeled nominal size range" and correspond to the sugar or sugar/starch beads of the invention. They can also be or be referred to as granules, particles, pellets or nonpareils and are from about 2 millimeters or about 10 mesh to about 0.2 millimeter or about 80 mesh, preferably from about 20 mesh to about 70 mesh, in diameter or longest dimension before coating. After coating the preferred diameter or longest dimension is from about 16 mesh to about 60 mesh.

The overcoat can be coated over the film by spraying the solution onto the substrate by using a vented pan or fluid bed coating unit with inlet air temperature of between 40°–80° C.

The dispersion of surface modified nanoparticles can be spray coated onto sugar spheres or onto a pharmaceutical excipient in a fluidized bed. The spray coating is accomplished by techniques well known in the art. Sugar spheres are described as containing "not less than 62.5 percent and not more than 91.5 percent of surose ($C_{12}H_{22}O_{11}$), calculated on the dried basis, the remainder consisting chiefly of starch" and as consisting of "approximately spherical particles of a labeled nominal size range" and correspond to the sugar or sugar/starch beads of the invention. They can also be or be referred to as granules, particles, pellets or nonpareils and are from about 2 millimeters or about 10 mesh to about 0.2 millimeter or about 80 mesh, preferably from about 20 mesh to about 70 mesh, in diameter or longest dimension before coating. After coating the preferred diameter or longest dimension is from about 16 mesh to about 60 mesh.

The composition can be formed into a capsule shell. The capsule shell of this composition of matter can be any pharmaceutically acceptable capsule shell but is preferably a gelating capsule shell and can be a soft gelatin capsule shell or a hard gelatin capsule shell but is preferably a hard gelatin capsule shell and is of suitable size for containing from about 0.5 milligram to about 700 milligrams of the composition of matter. Conventional machinery and technique are used in filling the capsule shells.

The particles of this invention can be prepared in a method comprising the steps of dispersing a drug substance in a liquid dispersion medium and applying mechanical means in the presence of grinding media to reduce the particle size of the drug substance to an effective average particle size of less than about 400 nm. The particles can be reduced in size in the presence of a surface modifier. Alternatively, the particles can be contacted with a surface modifier after attrition.

A general procedure for preparing the particles of this invention is set forth below. The drug substance selected is obtained commercially and/or prepared by techniques known in the art in a conventional coarse form. It is preferred, but not essential, that the particle size of the coarse drug substance selected be less than about 100 μm as determined by sieve analysis. If the coarse particle size of the drug substance is greater than about 100 μm, then it is preferred that the particles of the drug substance be reduced in size to less than 100 μm using a conventional milling method such as airjet or fragmentation milling.

The coarse drug substance selected can then be added to a liquid medium in which it is essentially insoluble to form a premix. The concentration of the drug substance in the liquid medium can vary from about 0.1–60%, and preferably is from 5–30%(w/w). It is preferred, but not essential, that the surface modifier be present in the premix. The concentration of the surface modifier can vary from about 0.1 to about 90%, and preferably is 1–75%, more preferably 20–60%, by weight based on the total combined weight of the drug substance and surface modifier. The apparent viscosity of the premix suspension is preferably less than about 1000 centipoise.

The premix can be used directly by subjecting it to mechanical means to reduce the average particle size in the dispersion to less than 400 nm. It is preferred that the premix be used directly when a ball mill is used for attrition. Alternatively, the drug substance and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the drug substance conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably, is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. We have found that zirconium oxide, such as 95% ZrO stabilized with magnesia, zirconium silicate, and glass grinding media provide particles having levels of contamination which are believed to be acceptable for the preparation of pharmaceutical compositions. However, other media, such as stainless steel, titania, alumina, and 95% ZrO stabilized with yttrium, are expected to be useful. Preferred media have a density greater than about 3 g/cm$^3$.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the drug substance. Processing temperatures of less than about 30° C.–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of drug substance and surface modifier can vary widely and the optimal amount of the surface modifier can depend, for example, upon the particular drug substance and surface modifier selected, the critical micelle concentration of the surface modifier if it forms micelles, etc. The surface modifier preferably is present in an amount of about 0.1–10 mg per square meter surface area of the drug substance. The surface modifier can be present in an amount of 0.1–90%, preferably 20–60% by weight based on the total weight of the dry particle.

As indicated by the following examples, not every combination of surface modifier and drug substance provides the desired results. Consequently, the applicants have developed a simple screening process whereby compatible surface modifiers and drug substances can be selected which provide stable dispersions of the desired particles. First, coarse particles of a selected drug substance of interest are dispersed in a liquid in which the drug is essentially insoluble, e.g., water at 5%(w/w) and milled for 60 minutes in a DYNO-MILL under the standard milling conditions which are set forth in Example 1 which follows. The milled material is then divided into aliquots and surface modifiers are added at concentrations of 2, 10 and 50% by weight based on the total combined weight of the drug substance and surface modifier. The dispersions are then sonicated (1 minutes, 20 kHz) to disperse agglomerates and subjected to particle size analysis by examination under an optical microscope (1000×magnification). If a stable dispersion is observed, then the process for preparing the particular drug substance surface modifier combination can be optimized in accordance with the teachings above. By stable it is meant that the dispersion exhibits no flocculation or particle agglomeration visible to the naked eye at least 15 minutes, and preferably, at least two days or longer after preparation.

The resulting dispersion of this invention is stable and consists of the liquid dispersion medium and the above-described particles. The dispersion of surface modified drug nanoparticles can be spray coated onto sugar spheres or onto a pharmaceutically excipient in a fluidbed spray coater by techniques well known in the art.

Pharmaceutical compositions according to this invention include the particles described above and a pharmaceutically acceptable carrier thereof. Suitable pharmaceutically acceptable carriers are well known to those skilled in the art. These include non-toxic physiologically acceptable carriers, adjuvants or vehicles for parenteral injection, for oral administration in solid or liquid form, for rectal administration, and the like. A method of treating a mammal in accordance with this invention comprises the step of administering to the mammal in need of treatment an effective amount of the above-described pharmaceutical composition. The selected dosage level of the drug substance for treatment is effective to obtain a desired therapeutic response for a particular composition and method of administration. The selected dosage level therefore, depends upon the particular drug substance, the desired therapeutic effect, on the route of administration, on the desired duration of treatment and other factors. As noted, it is a particularly advantageous feature that the pharmaceutical compositions of this invention exhibit unexpectedly high bioavailability as illustrated in the examples which follow. Furthermore, it is contemplated that the drug particles of this invention provide more rapid onset of drug action and decreased gastrointestinal irritancy.

It is contemplated that the pharmaceutical compositions of this invention will be particularly useful in oral and parenteral, including intravenous, administration applications. It is expected that poorly water soluble drug substances, which prior to this invention, could not have been administered intravenously, may be administered safely in accordance with this invention. Additionally, drug substances which could not have been administered orally due to poor bioavailability may be effectively administered in accordance with this invention.

The following composition in accordance with the first composition of matter aspect of the invention was prepared using the process aspect of the invention.

| Ingredient | Amount (kg.) |
| --- | --- |
| (5α,17α)-1'-(Methylsulfonyl)-1'H-pregn-20-yno[3,2-c]pyrazol-17-ol | 0.720 |
| Poloxamer 188, NF | 0.0900 |
| Polyethylene Glycol 3350, NF | 0.144 |
| Hydroxypropyl Methylcellulose, USP | 0.100 |

-continued

| Ingredient | Amount (kg.) |
|---|---|
| Sugar Spheres (30,35 mesh), NF | 0.450 |
| Purified Water, USP (removed during processing) | 2.46 |
| Total amount of dry ingredients | 1.500 |

A portion of this composition sufficient to provide 200 mg. of the steroid drug when filled into a hard gelatin capsule has the following composition:

| Ingredient | Mg./Capsule |
|---|---|
| (5α,17α)-1'-(Methylsulfonyl)-1'H-pregn-20-yno[3,2-c]pyrazol-17-ol | 200. |
| Poloxamer 188, NF | 25.0 |
| Polyethylene Glycol 3350, NF | 40.0 |
| Hydroxypropyl Methylcellulose, USP | 27.8 |
| Sugar Spheres (30,35 mesh), NF | 125. |
| Total Capsule Fill Weight | 418. |

The amount of drug in each capsule can be varied by varying the capsule fill weight, the amount of drug in the coating composition or the amount of coating composition coated onto the sugar or sugar/starch beads.

The composition of Example 1 was shown to have improved bioavailability over a conventional tablet composition of the same drug when compared in the dog. The following conventional tablet composition was prepared using a conventional table preparation method.

COMPARATIVE EXAMPLE

| Ingredient | Mg./Tablet |
|---|---|
| (5α,17α)-1'-(Methylsulfonyl)-1'H-pregn-20-yno[3,2-c]pyrazol-17-ol | 50.0 |
| Microcrystalline Cellulose, NF (Avicel pH 101) | 60.0 |
| Poloxamer 188, NF | 6.0 |
| Lactose, NF (Spray Dry) | 161.5 |
| Croscarmellose Sodium, FN (Ac-Di-Sol) | 15.0 |
| Magnesium, Stearate, NF | 1.5 |
| Providone, USP (PVP, K29-32) | 6.0 |
| Total | 300.0 |

Example 2—Preparation of a Pharmaceutical Composition

Two danazol dispersions were prepared by dissolving the PVP in water, dispersin the danazol substance, and milling by use of an agitating bead mill. The dispersion was milled to a final mean particle size of between 150–250 nm.

The pharmaceutical compositions were prepared by spray coating onto 5 different solid carrier (sugar beads, granular sugar, maltodextrin, Avicel pH 200 and Avicel CL 611) at varying levels of film dispersing agent (additive) and danazol content as follows.

TABLE 1

| Run # | Additives | Ratio of Additive to Danazol mg/gm | Grams Danazol/ $M^2$ Substrate | Substrate |
|---|---|---|---|---|
| 1 | Blg-1186-074 | low | low | Sugar Beads |
| 2 | Blg-1186-063 | high | high | Maltodextrin |
| 3 | Blg-1186-075 | low | low | Granular Sugar |
| 4 | Blg-1186-060 | high | high | Granualar Sugar |
| 5 | Blg-1186-069 | low | high | Sugar Beads |
| 6 | Blg-1186-072 | low | high | Avicel PH200 |
| 7 | Blg-1186-076 | low | low | Avicel PH200 |
| 8 | Blg-1186-073 | low | high | Avicel CL611 |
| 9 | Blg-1186-061 | high | high | Avicel PH200 |
| 10 | Blg-1186-071 | low | high | Maltodextrin |
| 11 | Blg-1186-065 | high | low | Granular Sugar |
| 12 | Blg-1186-077 | low | low | Avicel CL611 |
| 13 | Blg-1186-066 | high | low | Avicel PH200 |
| 14 | Blg-1186-068 | high | low | Maltodextrin |
| 15 | Blg-1186-078 | low | low | Maltodextrin |
| 16 | Blg-1186-059 | high | high | Sugar Beads |
| 17 | Blg-1186-067 | high | low | Avicel CL611 |
| 18 | Blg-1186-070 | low | high | Granular Sugar |
| 19 | Blg-1186-062 | high | high | Avicel CL611 |
| 20 | Blg-1186-064 | high | low | Sugar Beads |

The beads were tested for aqueous dissolution rate using a distek 6 vessel dissolution bath at 37° C., stirring at 300 rpm using paddles. Test media was 1 liter distilled water, equilibrated to 37° C. A stainless steel sampling probe was connected to tygon tubing, and an Ismatec SA peristaltic pump was used to control flow at ~0.18 ml/min. An inline 0.020 μm filter was used to remove particulate danazol and carrier debris and to ensure that danazol detected was actually in solution. A fresh filter was used for each test vessel. An amount of formulation equivalent to 20 mg of danazol was added to the test vessel and absorbance was monitored continuously for 20 minutes at 285 nm using a Waters 990 Photodiode Array system. The Waters 990 software was then used to form a rate plot by taking the differential of the absorbance vs. time curve. The maximum point on the rate plot was noted as the maximum rate of aqueous dissolution. The two Avicel carriers used in this study were both insoluble. The Avicel PH 200 was sized at approximately 60 μm (uncoated) and retained its form as an insoluble particle during the dissolution process. Because of it's size, a 10 μm solvent filter was placed on the end of the stainless steel sampling probe preventing clogging of the probe and the 0.020 μm in-line filter.

The Avicel CL 611 carrier was slightly smaller in size than the Avicel PH 200 in powder form, but immediately swelled in the presence of water to a size of approximately 60 μm. During the dissolution assay, the constant agitation and 37° C. temperature caused the Avicel CL 611 to break up into gelatinous particles in the 200 nm size range. All attempts to filter these particles failed. The gelatinous form of the Avicel CL 611 quickly and consistently clogged 0.2 μm and 0.1 μm filters placed inline before the 0.02 μm filter. For this reason, no aqueous dissolution data was obtained for the Avicel CL 611 formulations.

Sample preparation for Aqueous Redispersion Particle Size Analysis

—High Danazol Content Formulations: An amount of formulation equivalent to 50 mg of danazol was weighed into a 4 ml glass vial to which 1 ml of distilled water (room temperature) was added. The vial was capped and contents vortexed vigorously for 10 seconds. The prepared sample were then shaken at 300 rpm, 37° C. for 10 minutes using a LabLine Shaker Incubator, after which particle sizing was performed. All samples were prepared in duplicate.

—Low Danazol Content Formulations: An amount of formulation equivalent to 50 mg of danazol was weighed into a 20 ml glass scintillation vial to which 5 ml of room temperature distilled water was added. The vial was capped and contents vortexed vigorously for 10 seconds. The prepared samples were then shaken at 300 rpm, 37° C. for 10 minutes using a LabLine Shaker Incubator, after which particle sizing was performed. All samples were prepared in duplicate.

—Special note for Avicel PH 200 samples: The Avicel PH 200 carrier was removed by filtering through a 5 μm filter just prior to sizing.

—Special note for Avicel CL 611 samples: Since the Avicel CL 611 carrier itself was breaking into the nanometer size range of danazol, no usable redispersion sizing data were obtained for these formulations.

—Sizing using the Zetasizer III: Samples were diluted in filtered (0.45 μm) distilled water, and degassed before analysis. The AZ4 cell was used for all sizing procedures. Run time for size determinations was typically 120 seconds. Output from the Zetasizer III consisted of a mean particle size in nm and a 90%<value.

—Sizing using the Coulter N4MD: Samples were briefly vortexed then diluted 10 μl to ~15 ml in filtered (0.22 μm) deionized water. Diluted samples were shaken to obtain a homogeneous suspension. A 4.5 ml cuvette was cleaned and filtered (0.22 μm) deionized water, filled half way with filtered water, and sonicated for ~5 seconds to remove air bubbles. A minimal amount of the diluted sample was then added to impart a slight opaqueness to the contents of the cuvette. The cuvette was capped and inverted several times to allow proper mixing. The outside of the cuvette was siped completely dry and clean and placed into the sizing chamber which was maintained at 37° C. The viscosity setting was 0.693 cp and the refractive index was set to 1.331. The cuvette contents were adjusted as necessary to achieve a sample intensity in the range of $1.5 \times 10^5$ to $2.5 \times 10^5$ counts/second. Run time for particle sizing was typically 200 seconds. Output consisted of a mean particle size in nm, standard deviation, and a % Dust value.

Sugar Bead Formulations

Maximum aqueous dissolution rate values and redispersion particle sizing data are found in Table 2. The data clearly shows that the formulations containing the "high" additive ratio (Run #20 and #16) exhibited higher maximum aqueous dissolution rates and smaller particle sizes upon redispersion in water than their "low" additive ratio counterparts.

Granular Dextrose Formulations

Maximum aqueous dissolution rate values and redispersion particle sizing data are found in Table 3. On the granular matrix, there appears to be little difference in maximum aqueous dissolution rate among the 4 formulations. It can be seen, however, that the "high" additive ratio formulations (Run #11 and #4) resulted in smaller particle sizes upon redispersion compared to the two "low" additive ratio formulations.

Maltodextrin Formulations

Maximum aqueous dissolution rate values and redispersion particle sizing data are found in Table 4. The same pattern is observed here as in the granular dextrose formulations. The maximum aqueous dissolution rates are all high and similar. The "high" additive ratio formulations (Run #14 and #2) exhibit smaller redispersion particle sizes than the "low" additive formulations.

Avicel PH 200 Formulations

Maximum aqueous dissolution rate values and redispersion particle sizing data are found in Table 5. Results from the Avicel PH 200 matrix formulations closely mimic results of those formulations on the sugar bead matrix. The "high" additive ratio formulations (Run #13 and #9) exhibited higher maximum aqueous dissolution rates compared to the formulations containing the "low" additive ratio, and their redispersion particle sizes were much smaller as well, keeping with the trend observed in the previous three matrices.

TABLE 2

| Low/Low | Maximum Aqueous Dissolution Rate ($\times 10^{-5}$ AU/min) | Time to Maximum Rate (min) | Bead Formulations<br>Size (nm) | 90%<Value (nm) | Coulter N4MD Size (nm) | SD | % Dust |
|---|---|---|---|---|---|---|---|
| | | | Run #1 | | | | |
| | 5.3 | 3.6 | 299 | 670 | 371 | 180 | 17 |
| | 3.4 | 3.4 | 308 | 680 | 347 | 150 | 8 |
| | 4.6 | 3.8 | | | | | |
| Mean | 4.4 | 3.6 | 304 | | 359 | | |
| SD | 1.0 | 0.2 | 6 | | 17 | | |
| | | | Run #5 | | | | |
| | 3.1 | 4.4 | 271 | 580 | 274 | 45 | 18 |
| | 3.6 | 3.8 | 283 | 620 | >3 μm | | |
| | 3.1 | 4.2 | | | | | |
| Mean | 3.3 | 4.1 | 277 | | >3 μm | | |

TABLE 2-continued

Bead Formulations

| Low/Low | Maximum Aqueous Dissolution Rate ($\times 10^{-5}$ AU/min) | Time to Maximum Rate (min) | Size (nm) | 90%<Value (nm) | Coulter N4MD Size (nm) | SD | % Dust |
|---|---|---|---|---|---|---|---|
| SD | 0.3 | 0.3 | 8 | | | | |
| | | | Run #20 | | | | |
| | 6.4 | 2.0 | 223 | 430 | 268 | 100 | 0 |
| | 8.4 | 1.8 | 224 | 455 | 279 | 50 | 0 |
| | 8.7 | 2.4 | | | | | |
| Mean | 7.8 | 2.1 | 224 | | 274 | | |
| SD | 1.3 | 0.3 | 1 | | 8 | | |
| | | | Run #16 | | | | |
| | 8.0 | 2.6 | 213 | 410 | 240 | 37 | 6 |
| | 8.8 | 2.6 | 215 | 420 | 224 | 63 | 12 |
| | 7.4 | 2.8 | | | | | |
| Mean | 8.1 | 2.7 | 214 | | 232 | | |
| SD | 0.7 | 0.1 | 1 | | 11 | | |

TABLE 3

Granular Dextrose Formulations

| Low/Low | Maximum Aqueous Dissolution Rate ($\times 10^{-5}$ AU/min) | Time to Maximum Rate (min) | Size (nm) | 90%<Value (nm) | Coulter N4MD Size (nm) | SD | % Dust |
|---|---|---|---|---|---|---|---|
| | | | Run #3 | | | | |
| | 7.4 | 2.8 | 241 | 500 | 262 | 48 | 9 |
| | 6.6 | 2.8 | 239 | 520 | 255 | 66 | 7 |
| | 6.0 | 2.6 | | | | | |
| Mean | 6.7 | 2.7 | 240 | | 259 | | |
| SD | 0.7 | 0.1 | 1 | | 5 | | |
| | | | Run #18 | | | | |
| | 8.4 | 2.8 | 306 | 700 | 289 | 36 | 10 |
| | 5.8 | 2.8 | 315 | 710 | 272 | 50 | 16 |
| | 6.5 | 3.0 | | | | | |
| Mean | 6.9 | 2.9 | 311 | | 281 | | |
| SD | 1.3 | 0.1 | 6 | | 12 | | |
| | | | Run #11 | | | | |
| | 6.0 | 2.8 | 210 | 380 | 229 | 26 | 0 |
| | 7.0 | 3.0 | 205 | 400 | 224 | 62 | 8 |
| | 6.7 | 2.8 | | | | | |
| Mean | 6.6 | 2.9 | 208 | | 227 | | |
| SD | 0.5 | 0.1 | 4 | | 4 | | |
| | | | Run #4 | | | | |
| | 9.0 | 2.8 | 214 | 390 | 211 | 29 | 5 |
| | 7.2 | 2.6 | 216 | 420 | 240 | 42 | 1 |
| | 9.0 | 2.4 | | | | | |
| Mean | 8.4 | 2.6 | 215 | | 226 | | |
| SD | 1.0 | 0.2 | 1 | | 21 | | |

TABLE 4

Maltodextrin Formulations

| Low/Low | Maximum Aqueous Dissolution Rate ($\times 10^{-5}$ AU/min) | Time to Maximum Rate (min) | Size (nm) | 90%<Value (nm) | Coulter N4MD Size (nm) | SD | % Dust |
|---|---|---|---|---|---|---|---|
| | | | Run #15 | | | | |
| | 7.0 | 3.0 | 972 | 2200 | >3 μm | | |
| | 7.5 | 2.6 | 1282 | 3200 | >3 μm | | |
| | 7.5 | 2.7 | | | | | |
| Mean | 7.3 | 2.8 | 1127 | | >3 μm | | |
| SD | 0.3 | 0.2 | 219 | | | | |
| | | | Run #10 | | | | |
| | 8.0 | 2.3 | 653 | 1150 | >3 μm | | |
| | 7.8 | 2.5 | 530 | 1300 | >3 μm | | |
| | 7.0 | 2.6 | | | | | |
| Mean | 7.6 | 2.5 | 592 | | >3 μm | | |
| SD | 0.5 | 0.2 | 87 | | | | |
| | | | Run #14 | | | | |
| | 6.9 | 3.0 | 307 | 680 | 331 | 120 | 7 |
| | 6.5 | 2.8 | 326 | 720 | 286 | 35 | 5 |
| | 7.4 | 2.7 | | | | | |
| Mean | 6.9 | 2.8 | 317 | | 309 | | |
| SD | 0.5 | 0.2 | 13 | | 32 | | |
| | | | Run #2 | | | | |
| | 8.3 | 2.6 | 343 | 730 | 267 | 46 | 7 |
| | 9.0 | 2.4 | 247 | 520 | 281 | 39 | 0 |
| Mean | 8.7 | 2.5 | 295 | | 274 | | |
| SD | 0.5 | 0.1 | 68 | | 10 | | |

TABLE 4

Avicel PH200 Formulations

| Low/Low | Maximum Aqueous Dissolution Rate ($\times 10^{-5}$ AU/min) | Time to Maximum Rate (min) | Size (nm) | 90%<Value (nm) | Coulter N4MD Size (nm) | SD | % Dust |
|---|---|---|---|---|---|---|---|
| | | | Run #7 | | | | |
| | 5.0 | 3.1 | 250 | 490 | 278 | 41 | 0 |
| | 3.0 | 3.0 | 255 | 420 | 251 | 43 | 6 |
| Mean | 4.0 | 3.1 | 253 | | 265 | | |
| SD | 1.4 | 0.1 | 4 | | 19 | | |
| | | | Run #6 | | | | |
| | 3.2 | 3.2 | 254 | 525 | 254 | 44 | 5 |
| | 2.9 | 3.3 | 256 | 500 | 258 | 45 | 4 |
| Mean | 3.1 | 3.3 | 255 | | 256 | | |
| SD | 0.2 | 0.1 | 1 | | 3 | | |
| | | | Run #13 | | | | |
| | 6.2 | 3.0 | 214 | 400 | 219 | 21 | 4 |
| | 5.0 | 3.6 | 209 | 370 | 214 | 37 | 4 |
| Mean | 5.6 | 3.3 | 212 | | 217 | | |
| SD | 0.8 | 0.4 | 4 | | 4 | | |
| | | | Run #9 | | | | |
| | 6.5 | 3.0 | 229 | 370 | 212 | 29 | 5 |
| | 5.7 | 3.3 | 212 | 420 | 207 | 32 | 5 |
| Mean | 6.1 | 3.2 | 221 | | 210 | | |
| SD | 0.6 | 0.2 | 12 | | 4 | | |

Example 3—Preparation of Pharmaceutical Compositions and Test for Reconstitution A material having the following composition was formulated:

|  | % w.w |
|---|---|
| Drug Coat: | |
| 1. Danazol, USP | 15.1 |
| 2. Povidone (k15/17), USP | 4.52 |
| 3. Sodium Lauryl Sulfate, USP | 1.13 |
| 4. Purified Water, USP | — |
| Overcoat | |
| 5. Povidone (k15.17), USP | 0.847 |
| 6. Polyethylene Glycol 1000, NF | 0.148 |
| 7. Purified Water, USP | — |
| Carrier | |
| 8. Sugar Spheres (20–25 mesh), NF | 78.3 |
| Range (Drug Coat) | |
| Danazol/Povidone Ratio 10 to 1 to 1 to 1 | |
| Range Overcoat to Povidone 0.5 to 3.6 (w/w) | |

The pharmaceutical composition of Example 3 was used in vitro tests in fasted male beagle dogs and compared to a commercial Danocrine formulation as to relative oral bioavailability (mean AVC under the curve (AVC) at 20 mg/kg±Standard Error of the Mean (SEM). The oral AVC showed that the nanoparticulate Example 3 composition had a mean AVC. of 9860±2600 and 11988±3448 in 2 separate runs and the commercial Danocrine composition had an AVC ±SEM of 1076±391 (20mg/kg).

This indicated that the formulation of Example 3 achieved a 10× increase in absorption over that of the standard Danocrine formulation.

Example 4—Naproxen And Danazol Compositions

|  | A | B |
|---|---|---|
| Naproxen | 70.4 | 63.7 |
| Povidone | 4.22 | 3.82 |
| Sucrose | 21.1 | 19.1 |
| Sodium Lauryl Sulfate | 4.22 | 3.82 |
| Mannitol | — | 9.55 |

|  | C | D |
|---|---|---|
| Danazol | 40.0 | 20.0 |
| Povidone | 12.0 | 6.0 |
| Sodium Lauryl Sulfate | 3.0 | 1.5 |
| Dextrose | — | 72.5 |
| Maltodextran | 45.0 | — |

The reconstituted mean particle size was found to be less than 300 nm. The procedure used to determine the ease of reconstituting particles is as follows:

1. Weigh out appropriate amount of formulation, (eg, insoluble drug equivalent to 50 mg).

2. Add 1 to 10 ml of dispersion media (distilled water, 0.1NHcl, simulated gastric or intestinal fluid, etc.)

3. Vartex the mixture for 10 seconds.

4. Shake the prepared sample at 300 RPM, 37° C. for 10 minutes using a shako incubator such as a LabLine Shaker.

5. With a pipette draw off an appropriate amount of material from the preparation for particle sizing.

6. Size the resultant dispersion by using an appropriate technique such as a laser-light scattering, Franhaufa or disc centrifugation method.

It has been found that the PVP/PEG overcoat for compositions containing danazol, PVP and sodium lauryl sulfate coated on a bead, in particular, provides physical protection for the drug layer coated on the bead without inhibiting redispersion of the drug in aqueous media.

We claim:

1. A solid pharmaceutical composition comprising a capsule shell containing carrier particles, each particle having on its surface a film comprising nanoparticles of a low solubility drug associated with a steric stabilizer and a film dispersing agent, wherein dissolution of the solid pharmaceutical composition results in substantial redispersion of the drug nanoparticles.

2. A matrix of claim 1 wherein the low solubility drug has a solubility in water at ambient temperature of less than 1 part of drug in about 500 to greater than 1,000,000 parts by weight of the medium.

3. The matrix of claim 2 wherein the drug is selected from the group consisting of analgesics, anti-inflammatory agents, anthelminitics, anti-arrhythmic agents, antibiotics, anticoagulant, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, cardia inotropic agents, contrast media, corticosteroids, cough suppressants, diagnostic agents, diagnostic imaging agents, diuretics, dopaminergics, haemostatics, lipid regulating agents, muscle relaxants, parasympathomimetics, parathyroid calcitonin and biphosphonates, prostaglandins, radio-pharmaceuticals, sex hormones, anti-allergic agents, stimulants, anorectics, sypathomimetics, thyroid agents, vasodilators and xanthines.

4. The matrix of claim 3 wherein the drug is danazol, naproxen or cyclosporin.

5. The matrix of claim 1 wherein the steric stabilizer is a hydrophilic or amphophilic compound having steric stabilizing properties.

6. The matrix of claim 5 wherein the steric stabilizer is selected from the group consisting of gelatin, casein, lecithin, gum acacia, cholesterol, tragacanth, sorbitan esters, polyoxyethylene alkyl esters, polyoxyethylene caster oil derivatives, polyoxyethylene, sorbitan fatty acid esters, polyethylene glycols, polyoxyethylene stearates, carboxymethylcellulose calcium, carboxymethylcellulose sodium, methylcellulose, hydroxyethylcellulose, hydroxypropylcellulose, hydroxypropylmethylcellulose, phthalate, non crystalline cellulose, polyvinyl alcohol and polyvinylpyrrolidone.

7. The matrix of claim 6 wherein the steric stabilizer is polyvinylpyrrolidone.

8. The matrix of claim 1 wherein the film dispersing agent is a water soluble compound associated with the surface of the nanoparticle.

9. The matrix of claim 8 wherein the film dispersing agent is selected from the group consisting of mannitol, sodium lauryl sulfate, mono and di saccharides.

10. The matrix of claim 9 wherein the film dispersing agent is sodium lauryl sulfate.

11. The matrix of claim 1 wherein the matrix comprises about 0.1 to about 60% of a steric stabilizer and also 0.05 to about 60% of a film dispersing agent based on the weight of the drug.

12. The composition of claim 1 wherein the film comprises about 1 to 1200% by weight of the composition.

13. The composition of claim 12 wherein the film comprises about 0.1 to about 60% of a steric stabilizer and about 0.5 to about 60% of a film dispersing agent based on the weight of the drug.

14. The composition of claim 1 wherein the carrier particle is selected from the group consisting of sugar spheres, maltodextrin, microcrystalline cellulose, microcrystal cellulose/sodium carboxylmethylcellulose, granular dextrose, dicalcium phosphate, tricalcium phosphate, mono and disaccharides.

15. The composition of claim 14 wherein the carrier particle is selected from the group consisting of sugar spheres, 40–45 mesh, 30–35 mesh, 20–25 mesh, 18–20 mesh, 16–18 mesh, maltodextrin, dextrose, Avicel, mannitol, lactose, and dicalcium phosphate.

16. The composition of claim 15 wherein the carrier particle comprises sugar spheres having from 20 to 25 mesh.

17. A solid pharmaceutical composition comprising a capsule shell containing carrier particles, each particle having on its surface a film comprising nanoparticles of a low solubility drug associated with a steric stabilizer and a film dispersing agent, and an overcoat applied over said film comprising PVP/PEG, wherein dissolution of the composition results in substantial redispersion of the drug nanoparticles.

18. The composition of claim 17 wherein the low solubility drug has a solubility in water at ambient temperature of less than 1 part of drug in about 500 to greater than 1,000,000 parts by weight of the medium.

19. The composition of claim 17 wherein the drug is selected from the group consisting of analgesics, anti-inflammatory agents, anthelminitics, anti-arrhythmic agents, antibiotics, anticoagulant, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, cardia inotropic agents, contrast media, corticosteroids, cough suppressants, diagnostic agents, diagnostic imaging agents, diuretics, dopaminergics, haemostatics, lipid regulating agents, muscle relaxants, parasympathomimetics, parathyroid calcitonin and biphosphonates, prostaglandins, radio-pharmaceuticals, sex hormones, anti-allergic agents, stimulants, anorectics, sypathomimetics, thyroid agents, vasodilators and xanthines.

20. The composition of claim 17 wherein the drug is danazol, naproxen or cycloporin.

21. The composition of claim 17 wherein the steric stabilizer is a hydrophilic of amphophilic compound having steric stabilizing properties.

22. The composition of claim 17 wherein the steric stabilizer is selected from the group consisting of gelatin, casein, lecithin, gum acacia, cholesterol, tragacanth, sorbitan esters, polyoxyethylene alkyl esters, polyoxyethylene caster oil derivatives, polyoxyethylene, sorbitan fatty acid esters, polyethylene glycols, polyoxyethylene stearates, carboxymethylcellulose calcium, carboxymethylcellulose sodium, methylcellulose, hydroxyethylcellulose, hydroxypropylcellulose, hydroxypropylmethylcellulose, phthalate, non crystalline cellulose, polyvinyl alcohol and polyvinylpyrrolidone.

23. The composition of claim 17 wherein the steric stabilizer is polyvinylpyrrolidone.

24. The composition of claim 17 wherein the film dispersing agent is a water soluble compound associated with the surface of the nanoparticle.

25. The composition of claim 17 wherein the film dispersing agent is selected from the group consisting of mannitol, sodium lauryl sulfate, mono and di saccharides.

26. The composition of claim 17 wherein the film dispersing agent is sodium lauryl sulfate.

27. The composition of claim 17 wherein the matrix comprises about 0.1 to about 60% of a steric stabilizer and also 0.05 to about 60% of a film dispersing agent based on the weight of the drug.

28. A method of treating a mammal comprising the step of administering to the mammal an effective amount of the pharmaceutical composition of claim 17.

* * * * *